(12) United States Patent
Hoernig et al.

(10) Patent No.: US 10,307,118 B2
(45) Date of Patent: Jun. 4, 2019

(54) METHOD AND DEVICE FOR THE IMAGING SCANNING OF A FEMALE BREAST IN THE CONTEXT OF DIGITAL PROJECTIVE MAMMOGRAPHY OR TOMOSYNTHESIS

(71) Applicant: SIEMENS HEALTHCARE GMBH, Erlangen (DE)

(72) Inventors: Mathias Hoernig, Erlangen (DE); Michael Kelm, Erlangen (DE); Thomas Mertelmeier, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 267 days.

(21) Appl. No.: 15/272,698

(22) Filed: Sep. 22, 2016

(65) Prior Publication Data

US 2017/0079601 A1    Mar. 23, 2017

(30) Foreign Application Priority Data

Sep. 22, 2015  (DE) .................. 10 2015 218 155

(51) Int. Cl.
| | | |
|---|---|---|
| *A61B 6/00* | (2006.01) | |
| *A61B 6/02* | (2006.01) | |
| *A61B 6/04* | (2006.01) | |

(52) U.S. Cl.
CPC ............ *A61B 6/4233* (2013.01); *A61B 6/025* (2013.01); *A61B 6/4241* (2013.01); *A61B 6/481* (2013.01);
(Continued)

(58) Field of Classification Search
CPC .... A61B 6/00; A61B 6/02; A61B 6/04; A61B 6/025; A61B 6/4233; A61B 6/482;
(Continued)

(56) References Cited

U.S. PATENT DOCUMENTS 5,841,833 A    11/1998  Mazess et al.
9,025,855 B1    5/2015  Christoph et al.
(Continued)

FOREIGN PATENT DOCUMENTS

DE    102010000473 A1    8/2010

OTHER PUBLICATIONS

Hu, Y-H., et al., "The Effect of Amorphous Selenium Thickness on Imaging Performance of Contrast Enhanced Digital Breast Tomosynthesis", Breast Imaging, 11th International Workshop, IWDM 2012, Jul. 8-11, 2012, pp. 9-16, Springer-Verlag Berlin Heidelberg.
(Continued)

*Primary Examiner* — Jurie Yun
(74) *Attorney, Agent, or Firm* — Laurence Greenberg; Werner Stemer; Ralph Locher (57) ABSTRACT

A method image scans a female breast in the context of projective digital mammography or tomosynthesis with prefiltered x-ray radiation. From a single scanning two spatially superimposing images are created on the basis of pixel-by-pixel or pixel-group-by-pixel-group different x-ray energy spectra. An x-ray mammography system contains a radiator-detector system having an x-ray tube with a filter for generating a prefiltered x-ray radiation having a first radiation spectrum and a radiation detector containing a multiplicity of partial areas which generate individual image pixels. The radiator-detector system is configured to the effect that the partial areas receive pixel-by-pixel or pixel-group-by-pixel-group different radiation spectra, such that the two images from different x-ray spectra are received with a single scanning of the female breast. Ideally, the detector is a pixilated x-ray detector with a converting sensor layer that is divided into at least two sets of partial areas, the sets having different thicknesses.

16 Claims, 6 Drawing Sheets

(52) U.S. Cl.
CPC .............. *A61B 6/482* (2013.01); *A61B 6/502* (2013.01); *A61B 6/0414* (2013.01); *A61B 6/4035* (2013.01); *A61B 6/542* (2013.01)

(58) Field of Classification Search
CPC ....... A61B 6/502; A61B 6/481; A61B 6/4035; A61B 6/0414; A61B 6/4208; A61B 6/5229; G06T 2207/30068; G06T 2211/408; H01J 29/898; G01N 23/087
USPC ... 378/37, 62, 98.8, 98.9, 98.11, 98.12, 157, 378/158, 159
See application file for complete search history.

(56) References Cited

U.S. PATENT DOCUMENTS

| | | | | |
|---|---|---|---|---|
| 9,158,003 | B2* | 10/2015 | Kim | G01T 1/16 |
| 9,274,235 | B2* | 3/2016 | Kang | G01N 23/04 |
| 9,629,597 | B2* | 4/2017 | Vedantham | A61B 6/025 |
| 2013/0101082 | A1 | 4/2013 | Jordan et al. | |
| 2015/0117594 | A1 | 4/2015 | Pavlovich et al. | |

OTHER PUBLICATIONS

Xu, Q., et al., "Low-Dose X-ray CT Reconstruction via Dictionary Learning", IEEE Transactions on Medical Imaging, Sep. 2012, pp. 1682-1697, vol. 31, No. 9.

* cited by examiner

METHOD AND DEVICE FOR THE IMAGING SCANNING OF A FEMALE BREAST IN THE CONTEXT OF DIGITAL PROJECTIVE MAMMOGRAPHY OR TOMOSYNTHESIS

CROSS-REFERENCE TO RELATED APPLICATION

This application claims the priority, under 35 U.S.C. § 119, of German application DE 10 2015 218 155.3, filed Sep. 22, 2015; the prior application is herewith incorporated by reference in its entirety.

BACKGROUND OF THE INVENTION

Field of the Invention

The invention relates to a method for the imaging scanning of a female breast in the context of digital projective mammography or tomosynthesis and to an x-ray mammography system for the imaging scanning of a female breast in the context of digital projective mammography or tomosynthesis. Furthermore, the invention also relates to an x-ray detector containing a pixilated scanning structure.

It is generally known, in the context of digital mammography methods and tomosynthesis methods, both to provide support by contrast agents during the imaging and to use dual energy scanning in these methods, in order to obtain an improved imaging.

In contrast enhanced dual energy tomosynthesis of the Mamma (CEDET), typically after prior contrast agent injection a low-energy scan and a high-energy scan are in each case carried out while maintaining the breast compression. Analogously, a pair of high-energy and low-energy recordings is created for contrast enhanced dual energy mammography (CEDEM). The different x-ray energy spectra used here are attained by different filtering and/or different acceleration voltages. Correspondingly, between two recordings the x-ray filter is changed and/or the acceleration voltage of the x-ray tube is changed.

For such applications, use is usually made of flat detectors operating either as direct converters (x-ray-electrons/holes) or as indirect converters (x-ray-light-electrons).

The problem of such methods and devices is that generating separate high-energy and low-energy recordings costs time in which:
a) the patient moves, for example on account of his/her respiration;
b) the contrast agent moves or its concentration and distribution change;
c) the application possibly has to be restricted to specific views, such as, for example, CC (=cranio caudal) or MLO (=medio lateral oblique), of a breast since the washout phase of the contrast agent is advanced; and
d) doubled volumes of data have to be managed, particularly in the case of tomosynthesis, which is more data intensive.

SUMMARY OF THE INVENTION

Therefore, it is an object of the invention to find a method and a device which make it possible to prevent the disadvantages of an excessively long duration of two scans.

This object is achieved by means of the features of the independent patent claims. Subordinate claims relate to advantageous developments of the invention.

The inventors have recognized that it is possible to shorten the long duration of a double scan by virtue of the fact that during a single scan, absorption information regarding at least two different energy spectra is simultaneously collected.

A particular advantage is afforded here by the simultaneity of the recordings, as a result of which the radiologist acquires a better temporal correlation with respect to the enhancement peak by the applied contrast agent for a plurality of views of one or both breasts and a better intensity assignment of the enhancements is thus possible.

This collection of absorption information of at least two different energy spectra can be achieved according to the invention first in that a first set of partial areas of the detector—including, of course, the scan object situated in front—is irradiated with a first x-ray spectrum and a second supplementary set of partial areas is irradiated with a different energy spectrum. In the context of the invention it is also possible to use more than two sets of partial areas in order to realize a multi-energy scan instead of a dual-energy scan. The partial areas correspond here to individual pixels or pixel groups, such that overall it is possible to collect a plurality of images from the pixels of a respective energy spectrum. Gaps in the pixel division can be bridged by interpolation, for example.

Second, even without intervention in the irradiating x-ray energy spectrum, absorption information of at least two different energy spectra can be obtained by locally varying only the absorption spectrum of the radiation-detecting sensor. In this regard, for example, an increase in the selenium layer (a-Se) from 200 µm to 300 µm in a direct conversion detector produces a significant improvement in the detective quantum efficiency (DQE) for high-energy recordings. It can be deduced from this that in the thinner sensor layer the complete energy of the high-energy photons is not captured and an energy-dependent absorption spectrum of the incident radiation depending on the sensor layer thickness thus results.

On account of the different x-ray energies of both recordings or projection recordings, the radiation absorption of present-day detectors, such as, for example, direct conversion x-ray flat detectors composed of a-Se, is suboptimal since they are optimized either specifically for standard applications in the low-energy range or specifically for the high-energy range in terms of the selenium layer thickness.

If consideration is given to the first embodiment variant of the invention with the use of a spatially different x-ray filter upstream of the scan object and the detector, that is to say a spatially spectral x-ray filter, the following observations become evident.

According to the invention, it is possible to create, preferably contrast agent enhanced, dual energy mammography in a single x-ray recording and with a single x-ray image to be read out by virtue of the fact that an x-ray filter that carries out separation for at least two x-ray energy spectra is positioned between radiator and detector, the filter acting spatially differently, that is to say differently in different partial regions of a detector or of the radiation beam used. Such a filter is referred to hereinafter as "spatially spectral x-ray filter".

The spatially spectral x-ray filter preferably consists of a greatly absorbent material such as titanium and has a 3D structure preferably manifested as checkered thickness structures, wherein the larger thickness is used for the high-energy separation (radiation hardening) and the thin structure in the radiation direction is used for the low-energy separation. In this case, the area distribution of high-energy and low-energy filter is preferably of equal magnitude.

According to the invention the spatially spectral x-ray filter can:
a) have thickness structures by variation of one material; or
b) have thickness structures by variation of a plurality of materials; or
c) have a largely uniform total filter thickness by coupling of a plurality of materials or alloys. Edges that generate scattered radiation are omitted here.

The spatially spectral x-ray filter can be produced for example by a 3D print method or etching method.

A positioning of the spatially spectral x-ray filter at a fixed distance from the x-ray source is additionally proposed, wherein this should be coupled to the movement of the x-ray source.

It is additionally proposed, in an alternative configuration, to embody the x-ray filter with a large area and to integrate it in the compression plate or to arrange it a few millimeters to a few centimeters above the plate compressing the breast. In order to avoid effects such as minimal decompression or jolts, pressures during the image recordings, a separate suspension on the compression plate mount or an entirely separate suspension can be realized.

The invention additionally proposes that a high-energy spectrum, preferably with an acceleration voltage of the x-ray tube of 42 kVp to 49 kVp, is used for the scanning.

Alternatively, within a scan, that is to say a scanning or a tomo-projection, the acceleration voltage at the x-ray tube used can be changed, that is to say pulsed, at least once between a low acceleration voltage in the range of 23 kVp to 35 kVp and a high acceleration voltage in the range of 42 kVp to 49 kVp. In this case, the length of a partial pulse should preferably be less than 50 msec.

Alternatively, it is proposed, within a recording, to increase the acceleration voltage largely linearly between a low and a high voltage value in a ramp-like fashion over the total pulse length.

Each recorded x-ray image or each recorded angle projection image can then be analyzed by the spatial structure known from a preceding calibration process and be decomposed into its spectral components. For this purpose, methods of "compressed sensing" are suitable, in which the spectral resolution is generated with the aid of spatial smoothness assumption at the expense of the spatial resolution. As a result, this gives rise to at least two spectrally separated partial images each having half the spatial resolution, which can then be used for a weighted subtraction for creating a recombined result image. The somewhat lower spatial resolution is noncritical and acceptable for the detection of contrast agent enhanced regions.

Analogously, for the tomosynthesis two volumes can be created and, if appropriate, registered and a recombined volume can subsequently be calculated.

In addition, a calibration method is also proposed in which the structured x-ray filter is positioned at defined distances with respect to the detector, preferably between 20 mm and 120 mm, in a manner coupled to the radiator. In this case, the calibration is effected in such a way that each recording without an object is created in a pulsed manner with at least two x-ray voltages. Preferably, a series of recordings is created for a breast-thickness-dependent pulse length variation. These data can be stored in the recording system. In patient operation, the x-ray filter is then always moved to a previously calibrated position and operated in a calibrated mode.

In a further alternative embodiment, the structured x-ray filter can be formed from at least two materials, for example from two of the materials Rh, Al, Cu, Ti, or two combinations of the materials, and can contain regions/structures for a plurality of energy spectra to be formed thereby.

The advantage of this first embodiment variant of the method for creating contrast medium enhanced x-ray images for spectral 2D and 3D breast imaging is that:
an additional low-energy scan is obviated;
the recombined 2D result image has no motion artifacts;
the procedure (2D, 3D) is faster and saves time and patient comfort is increased as a result;
the recording time for CEDET is reduced; and
the patient dose is reduced.

Regarding the second embodiment variant of the invention with the use of converting sensor materials having different thicknesses in the detector for achieving a spatially different absorption spectrum with which different x-ray energies are detected to different extents, it is proposed that the x-ray detector has a thickness structure in the material that converts the x-ray radiation into light or free charge. Wherein preferably at least one of the following features is present: the structure of the converting sensor layer in the radiation direction has at least two different thicknesses, the thicknesses of the sensor layer are chosen such that depending on the x-ray radiation used, firstly the high-energy part of the x-ray spectrum is at least predominantly not absorbed in the regions of small thickness and thus yields no signals, while the low-energy portion of the x-ray spectrum is already considerably to predominantly absorbed there and yields corresponding signals, and second the high-energy part of the x-ray spectrum is significantly attenuated in the thicker layer and correspondingly yields signals there, while the low-energy part of the spectrum is attenuated here as well and a signal portion in addition to the high-energy portion arises. In the case of a low-energy recording, both detector thickness regions yield imaging signals since the x-ray quanta are absorbed and converted in the converter material.

The at least two thicknesses are preferably distributed in equal proportions in the structure, preferably are arranged in a checkered fashion or in the form of lines, the thickness structures are produced in a structured carrier material (e.g. glass) to which the (one) converting layer is applied. The thickness structures are produced in a layer between converter layer and carrier material (e.g. by photodiodes and/or TFTs situated there). The thickness structure is produced by 3D printing, lithography or etching. The invention relates to an x-ray detector which is preferably not a "counting" detector but rather a directly or indirectly energy-integrating detector, such as, for example, a-Si, a-Se or CMOS detectors.

It may be advantageous if the x-ray detector contains a pixel by pixel gain circuit which is coupled to the thickness structure of the converting sensor layer, such that switchable amplifier stages are provided at least regionally for the regions of the thicker and thinner converter layers. It is thus possible almost to suppress the high-energy signals in the thinner regions by the gain step being set to be small and thus only the desired high-energy portion being counted. Alternatively, the low-energy signal portions of a high-energy recording which are imaging in the thin converter layer can also be amplified in a targeted manner.

In conjunction with beam hardening x-ray filters, a combined low/high-energy image can be generated at high x-ray energies since the high-energy quanta are predominantly absorbed in the regions having a thicker structure.

Depending on the production method, the size of the individual "checkerboard fields" can vary and be formed according to the size of an individual pixel or a plurality of binned pixels (2×2 or 3×3). Alternative spatial structures or the use of more than two energetically distinguishable pixel types are likewise possible.

In conjunction with low-energy x-ray radiation, the detector can also be used for conventional mammography and tomosynthesis recordings. Possible pixel-dependent intensity differences can be compensated for here in a calibration step.

Besides mammography, other fields of application in x-ray-based medical imaging are also possible. For example, for separating soft tissue and bone in radiography including without a contrast agent.

The advantage of the x-ray detector having energy-selective absorption behavior for the dual-energy imaging is that:
non-counting x-ray detectors can be used,
the DQE for high-energy applications is better,
high-energy quanta are not imaging in regions of thin converter layers and thus the efficiency of the iodine imaging is increased,
as a result of the rear-side arrangement of the thickness structure even in the case of angle projections such as tomosynthesis no scattered radiation and absorption effects occur, and
the detector can also be employed for the use of conventional (single-energy) recordings.

Both variants described above generate image data which are temporally congruent and likewise spatially congruent in their limits. For the calculation of a respective low-energy and high-energy image, the pixels respectively missing can be supplemented by, preferably bilinear, interpolation. Alternatively, it is also possible to use more powerful methods of "compressed sensing" such as e.g. methods based on Markov random fields or on total variation.

By way of example, mention is made below of the method of spectrally segregating an absorption image with information regarding N different spectra—here caused by N acceleration voltages at the x-ray tube (=anode voltages), by means of a compressed sensing method.

The recording of an object (breast) with the spatially spectral x-ray filter with the use of N anode voltages generates an absorption image I(x,y) that can be regarded as a superimposition of a plurality of spectral images. From the calibration process, the N absorption images ($K_n$) are additionally known which were recorded by the spatially spectral x-ray filter without an object, principally without a breast, for each of said N anode voltages. The superimposed absorption image I(x,y) can thus be modeled as a sum of the absorption images of the x-ray filter and the recorded object:

$$a) I = i(x,y) = \Sigma_{n=1}^N (I_n(x,y) + K_n(x,y)) \quad (1).$$

The $K_n(x,y)$ and, apart from noise to be modeled, the superimposed absorption image I are known here. The spectral individual components $I_n = I_n(x,y)$ are to be extracted, however. These can be determined from the above system, however, only under additional assumptions, a so-called regularization term $R(I_1, \ldots, I_N)$ or "prior term". Let J=J(x,y) be the noisy recording of the superimposed absorption image I. The spectral individual components can then be determined from the following optimization problem:

a)
$$(I_1, \ldots, I_N) = \underset{(I_1, \ldots, I_N)}{\mathrm{argmin}} [D(J, I) + \lambda R(I_1, \ldots, I_N)]. \quad (2)$$

Wherein the parameter $\lambda$ sets the weighting between the data term D(J,I) and the regularization term $R(I_1, \ldots, I_N)$.

In this case, the data term is dependent on the assumed noise. Inter alia, the following data terms are expedient in the context of x-ray recordings, wherein the latter are based on the assumptions of noise with Gaussian or Poisson distribution:

$$D(J,I) = \Sigma_x \Sigma_y (I(x,y) - J(x,y))^2 \text{(Gaussian distribution)} \quad (3)$$

$$D(J,I) = \Sigma_x \Sigma_y (I(x,y) - J(x,y) \ln I(x,y))^2 \text{(Poisson distribution)} \quad (4).$$

With the regularization term $(I_1, \ldots, I_N)$, smoothness assumptions are modeled which effectively bring about a reduction of the spatial resolution. For this purpose, by way of example, a measure of the smoothness of all the individual components $I_n(x,y)$ is defined:

$$a) R(I_1, \ldots, I_N) = \Sigma_{n=1}^N \lambda_n G(I_n) \quad (5)$$

wherein the measure of the smoothness can be set individually for each component by means of $\lambda_n$. As a measure of the smoothness, here the total variation (TV) is suitable, for example, which is defined in its isotropic form as $$G(I_n) =$$
$$TV(I_n) = \int\int \|I_n(x,y)\| dx dy \cong \sum_i \sum_j \sqrt{(\Delta_x I_n(i,j))^2 + (\Delta_y I_n(i,j))^2}$$

that is to say the integral (or the sum) of the gradient magnitudes that occur.

Alternatively, other measures of smoothness can also be used. With the aid of the Markov random fields, a different class of cost functions can be defined as $$G(I_n) = \sum_{(i,j)\in \aleph} K_{ij}(I_n)$$

wherein here a sum of pixel pairs of $I_n$ is formed, the correspondence of which is assessed according to the defined neighbor system $\aleph$. Convex functions suitable for this are e.g.

$$K_{ij}(I_n) = (I_n(x_i, y_i) - I_n(x_j, y_j))^2 \quad (Gaussian \text{ distribution})$$

$$K_{ij}(I_n) = |I_n(x_i, y_i) - I_n(x_j, y_j)| \quad (\text{Absolute}/L1\text{-}norm)$$

$$K_{ij}(I_n) = \begin{cases} (I_n(x_i, y_i) - I_n(x_j, y_j))^2 & |I_n(x_i, y_i) - I_n(x_j, y_j)| < \rho \\ |I_n(x_i, y_i) - I_n(x_j, y_j)| & \text{else} \end{cases} \quad (Huber)$$

Instead of first differences and gradients, it is also possible, of course, to use second-order and higher-order differences and derivatives for the formation of smoothness assumptions.

In equation (1), moreover, a differently configured measure of smoothness can also be used for each component $I_n$.

With the aid of additional terms in equation (5), the regularization term $R(I_1, \ldots, I_N)$ can also define costs between the individual components $I_n(x,y)$ to be determined. It would also be possible for the components of adjacent energy bands to be intended to be similar, which can in turn be expressed by way of quadratic differences, i.e.

$$R(I_1, \ldots, I_N) = \cdots + \Sigma_{(i,j)} \mu_{ij} \|I_i - I_j\|^2 i. \quad (6).$$

Wherein $\mu_{ij}$ weights the differences between the components of the adjacent energy i and j.

In accordance with these insights, the inventors propose a method for the imaging scanning of a female breast in the context of digital mammography or tomosynthesis with prefiltered x-ray radiation, wherein from a single scanning at least two spatially superimposing images are created on the basis of pixel by pixel or pixel group or by pixel group different x-ray energy spectra.

In accordance with a first embodiment variant of this method, the at least two images are generated on the basis of different x-ray energy spectra on account of different radiation spectra of x-ray radiation impinging on the pixel-forming detector elements of a detector.

In accordance with a second embodiment variant, the at least two images can be generated on the basis of different x-ray energy spectra on account of different absorption spectra in the sensor layers of the pixel-forming elements of a detector.

The embodiments mentioned above can also be combined, such that it is also proposed that the at least two images are generated on the basis of different x-ray energy spectra on account of a combination of different spectra of x-ray radiation impinging on the pixel-forming elements of a detector and different absorption spectra in the pixels of a detector.

Regarding the embodiment variants in which locally and spectrally different absorption behaviors are used in the detector, according to the invention the spectrally different absorption of impinging x-ray radiation on the pixel-forming elements of the detector can be generated by sensor layers configured with different thicknesses and/or by different sensor materials.

In methods with different filtering, the different radiation spectra of impinging x-ray radiation on the pixel-forming detector elements of the detector are generated by, pixel by pixel or pixel group by pixel group, filter layers configured with different thicknesses, and/or different filter materials.

In a further embodiment variant of the method according to the invention, the at least two images can also be generated on the basis of different x-ray energy spectra by a variation of the x-ray spectrum during the scanning, wherein preferably this variation of the x-ray spectrum can be effected by multiple, preferably pulsed, preferably ramped or sinusoidal, variation of the acceleration voltage during the scanning.

The method according to the invention is also suitable in particular for an imaging accompanied by contrast agent administration.

Besides the method according to the invention, the inventors also propose an x-ray mammography system for the imaging scanning of a female breast in the context of contrast agent enhanced digital mammography (CEDEM), or a tomosynthesis (CEDET). The system includes the following features:
a radiator-detector system containing an x-ray tube with a filter for generating a prefiltered x-ray radiation having a first radiation spectrum; and
a radiation detector in the radiator-detector system, the radiation detector containing a multiplicity of partial areas which generate individual image pixels, and wherein the radiator-detector system is configured to the effect that the partial areas receive pixel by pixel or pixel group by pixel group different radiation spectra, such that at least two imagings from different x-ray spectra are received with a single scanning of the female breast.

In a first embodiment variant of the x-ray mammography system, the partial areas of the detector can be covered by pixel by pixel or pixel group by pixel group differently absorbent radiation filters in relation to the prefiltered x-ray radiation and thereby generate different x-ray energy spectra.

Additionally or supplementarily, the partial areas of the detector can have, pixel by pixel or pixel group by pixel group, sensor layers configured with different thicknesses, and thereby detect the impinging radiation with different absorption spectra.

Also proposed is an x-ray mammography system for the imaging scanning of a female breast in the context of digital mammography (CEDEM) or tomosynthesis (CEDET), the system contains a programmable control device for the acceleration voltage of an x-ray tube. A program is stored and is executed during operation, which program performs one of the methods according to the invention as described here.

Supplementarily to the x-ray mammography system, an x-ray detector is also proposed, in particular for use with the method according to the invention and the x-ray mammography apparatus according to the invention, having a pixilated scanning structure, wherein a sensor layer which converts the x-ray radiation into light or charge is divided into at least two sets of partial areas, said sets having different thicknesses. Preferably, the subdivision of the detector area into the partial areas is effected in a checkered or line-like fashion, wherein this division is implemented preferably in a finely structured fashion with structures in the range of individual pixels up to a dimension of two, three or four pixel widths. This therefore means pixel groups of 1×1 to 4×4 pixels in the case of a checkered configuration or pixel line groups having widths of 1 to 4 pixels in the case of line-like structuring.

Furthermore, a sensor layer having different thicknesses can preferably be arranged on that side of the detector which faces the radiation.

Preferably, the different thicknesses of the sensor layer are formed by a thickness structure, wherein the latter is produced by filling a structure of a carrier material.

On account of the pixel by pixel or pixel group by pixel group different thicknesses, a corresponding difference in the charge absorption properties should be expected, thus resulting in different signal intensities. This is remedied by a gain correction which is integrated into the detector electronics and which is coupled to the thickness structure. Alternatively, a downstream image preprocessing can also compensate for such differences.

Other features which are considered as characteristic for the invention are set forth in the appended claims.

Although the invention is illustrated and described herein as embodied in a method and a device for the imaging scanning of a female breast in the context of digital projective mammography or tomosynthesis, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

The following reference signs are used consistently throughout the figures: 1: mammography system; 2: housing/stand; 3: swivel axis; 4: swivel arm; 5: x-ray tube; 6: spatially structured spectral filter; 6.1-6.3: fields of different thicknesses; 7: detector; 7.1: carrier layer/TFT panel; 7.2: photodiodes; 7.3: spacer elements; 7.4: intermediate layer; 7.5: converting sensor layer; 8: upper compression plate; 9: cover/lower compression plate; 10: drive unit of the upper compression plate; 11: beam; 12: computing and control unit; 13: memory; 14: programs.

Figure 1:
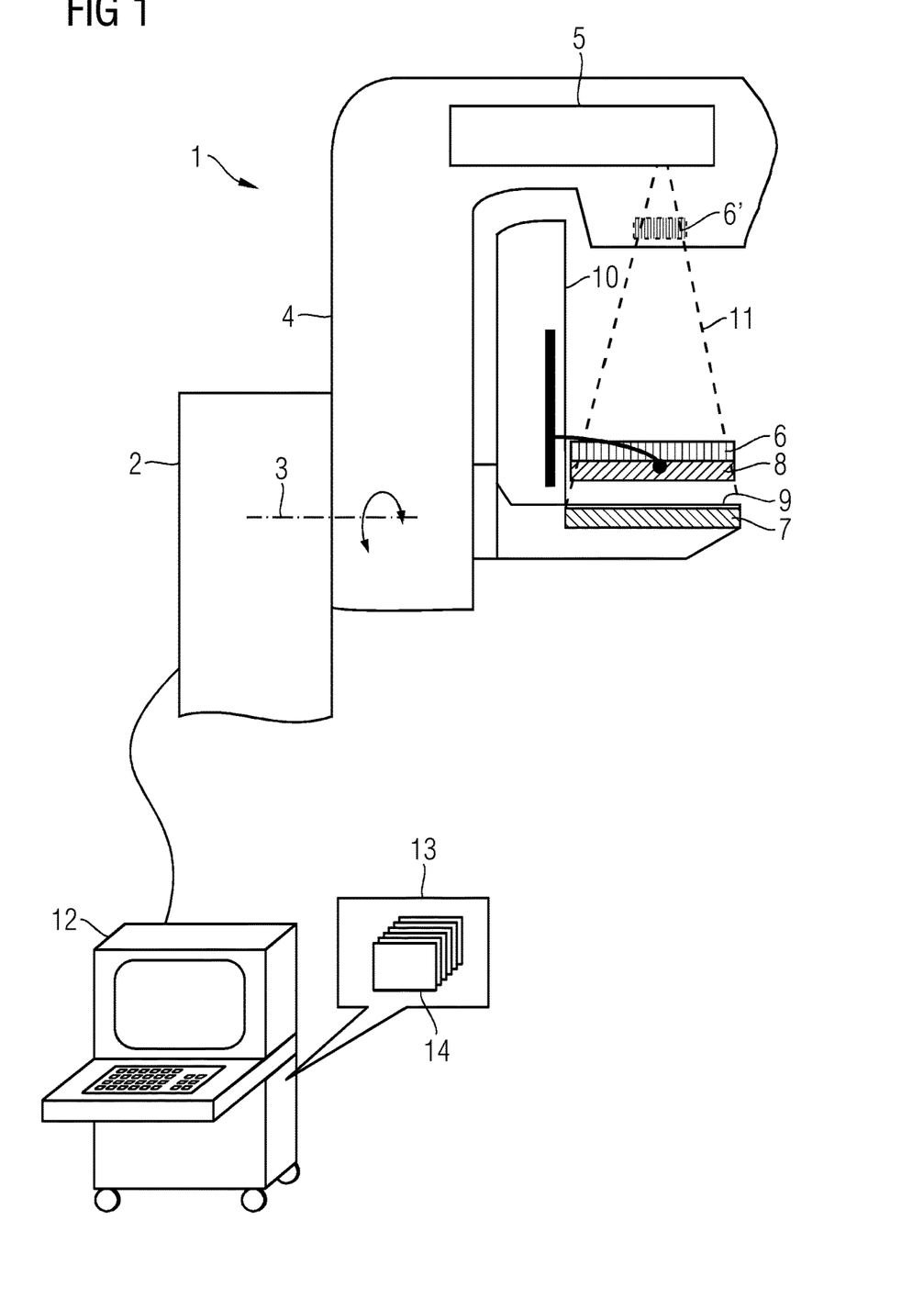
FIG. 1 is an illustration showing the construction of an x-ray system for generating projective or tomosynthetic image data of a female breast with a spatially structured spectral filter directly above an upper compression plate (alternatively in the region of the x-ray tube) for generating spatially different radiation spectra according to the invention.

Referring now to the figures of the drawings in detail and first, particularly to FIG. 1 thereof, there is shown, in a schematic side view, a mammography system 1 according to the invention for creating a digital mammographic two-dimensional or three-dimensional representation (projective or tomosynthetic representation) of a female breast using a spectral filter configured in a checkered fashion. In this case, a swivel arm 4, mounted such that it can swivel about an axis 3, is situated on a housing or stand 2 (not fully illustrated), an x-ray tube 5 being arranged in the swivel arm at the top in the head. A flat detector 7 is arranged below the x-ray tube 5, which has a prefilter, which is not illustrated in more specific detail and acts over the entire beam path, a cover 9 of the flat detector being embodied simultaneously as a lower compression plate. An upper compression plate 8 is situated above the lower compression plate. A spectral filter 6 according to the invention is situated directly above the compression plate 8, which spectral filter, in a manner subdivided in a checkered fashion, hardens to locally different extents a radiation that passes through.

In addition, a filter 6' arranged directly at the x-ray tube 5 as an alternative to the spectral filter 6 is also shown. Both arrangements are possible within the scope of the invention.

From the x-ray tube 5, to put it more precisely from the focus generated there, a beam 11 extends to the flat detector 7. During the scan the swivel arm 4 is moved about the swivel axis 3, such that the breast situated between the compression plates is transilluminated from a multiplicity of projection angles and projective or tomosynthetic representations can be generated therefrom. The scanning procedure, if appropriate with variation of the acceleration voltage according to the invention, is controlled by a control and computing unit 12, which is connected to the x-ray system and has a memory 13 and programs 14 stored therein, which programs are executed during operation. The data acquisition via the detector 7 and the data conditioning including the calculation according to the invention of projective and tomosynthetic recordings on the basis of different energy spectra are also performed with the programs 14.

Figure 2:
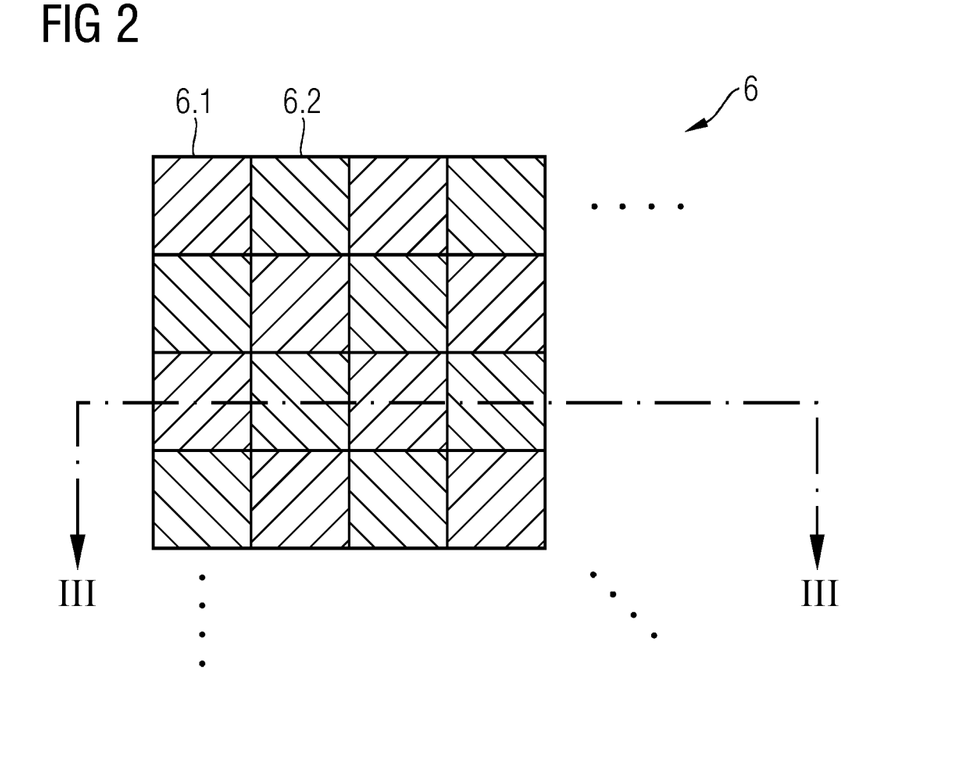
FIG. 2 is a plan view of a spatially structured spectral filter having two different thicknesses including section III-III.
Figure 3:
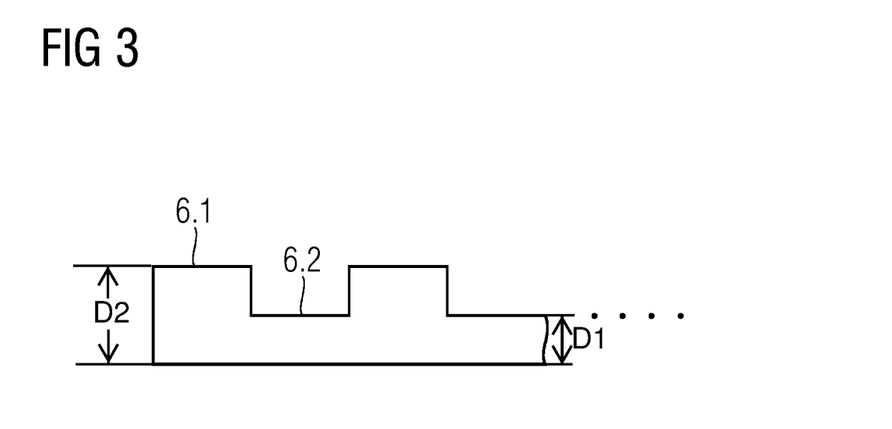
FIG. 3 is a sectional view taken along the section line III-III shown in FIG. 2.

FIG. 2 shows at the top a schematic plan view of an excerpt from a spatially structured spectral filter 6, which is embodied in a checkered fashion here by way of example and has two different material thicknesses on the distributed different fields 6.1 and 6.2. In this case, identical hatchings correspond to identical field types. These different material thicknesses D1 and D2 which are assigned to the fields 6.1 and 6.2 and which extend in the radiation direction are illustrated again in FIG. 3 with the section III-III illustrated there. However, it is explicitly pointed out that it also lies within the scope of the invention, instead of or in addition to the material thickness, also to carry out a structuring by different filter materials, wherein in particular it is also possible to use filter materials which are simultaneously used as contrast agent in the examination.

Figure 4:
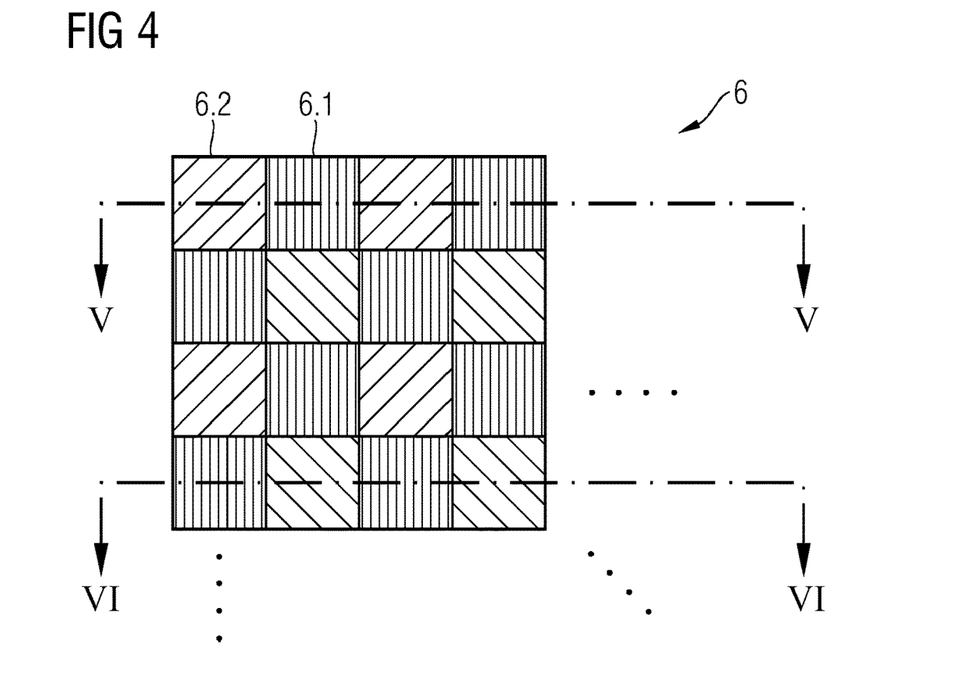
FIG. 4 is a plan view of a spatially structured spectral filter having three different thicknesses including sections V-V and VI-VI.

FIG. 4 shows, in a manner similar to FIG. 2, a schematic plan view of an excerpt from a spatially structured spectral filter 6, although the spatial structure now has three different types of fields 6.1, 6.2 and 6.3, which are in each case hatched identically. It is pointed out that a checkered pattern is chosen here only for the sake of simplified illustration, but any other distribution patterns, for example honeycomb patterns or random patterns, are considered to be included within the scope of the invention.

Figure 5:
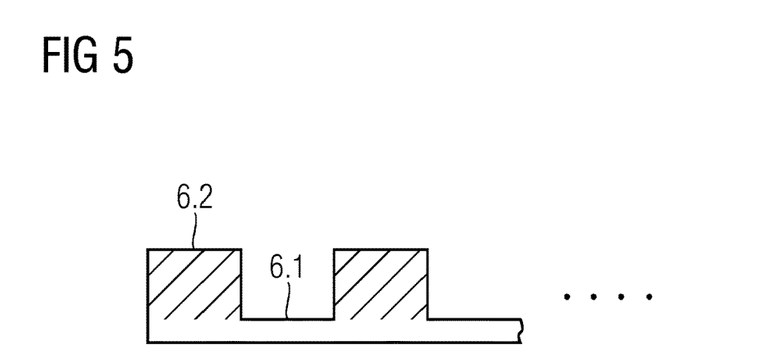
FIG. 5 is a sectional view taken along the section line V-V shown in FIG. 4.
Figure 6:
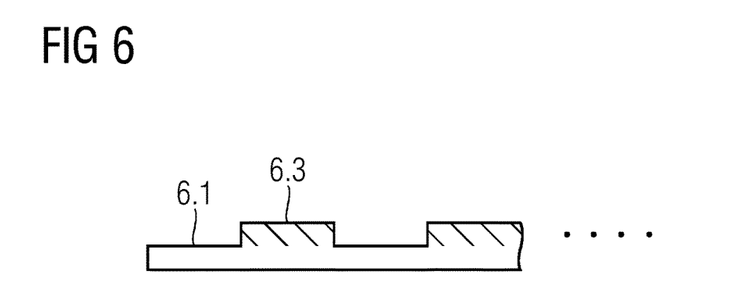
FIG. 6 is a sectional view taken along the section line VI-VI shown in FIG. 4.

Below the plan view of the spatially structured filter 6, FIGS. 5 and 6 show two sections V-V and VI-VI. A special feature of the filter 6 here is that not just three different material thicknesses were realized in the filter, rather the three field types also consist of different material combinations. In this regard, each of the sections reveals at the bottom a common carrier area (without hatching) on which respectively—illustrated by the hatching—different materials are applied with different material thicknesses. As a result, the different spectral filtering is influenced not only by the material thickness but also by the different materials themselves in a desired manner. A possible use of the contrast material itself applied as contrast agent in the examination has already been pointed out above. The production of such filters is possible for example by means of etching methods or modern 3D printing methods.

Figure 7:
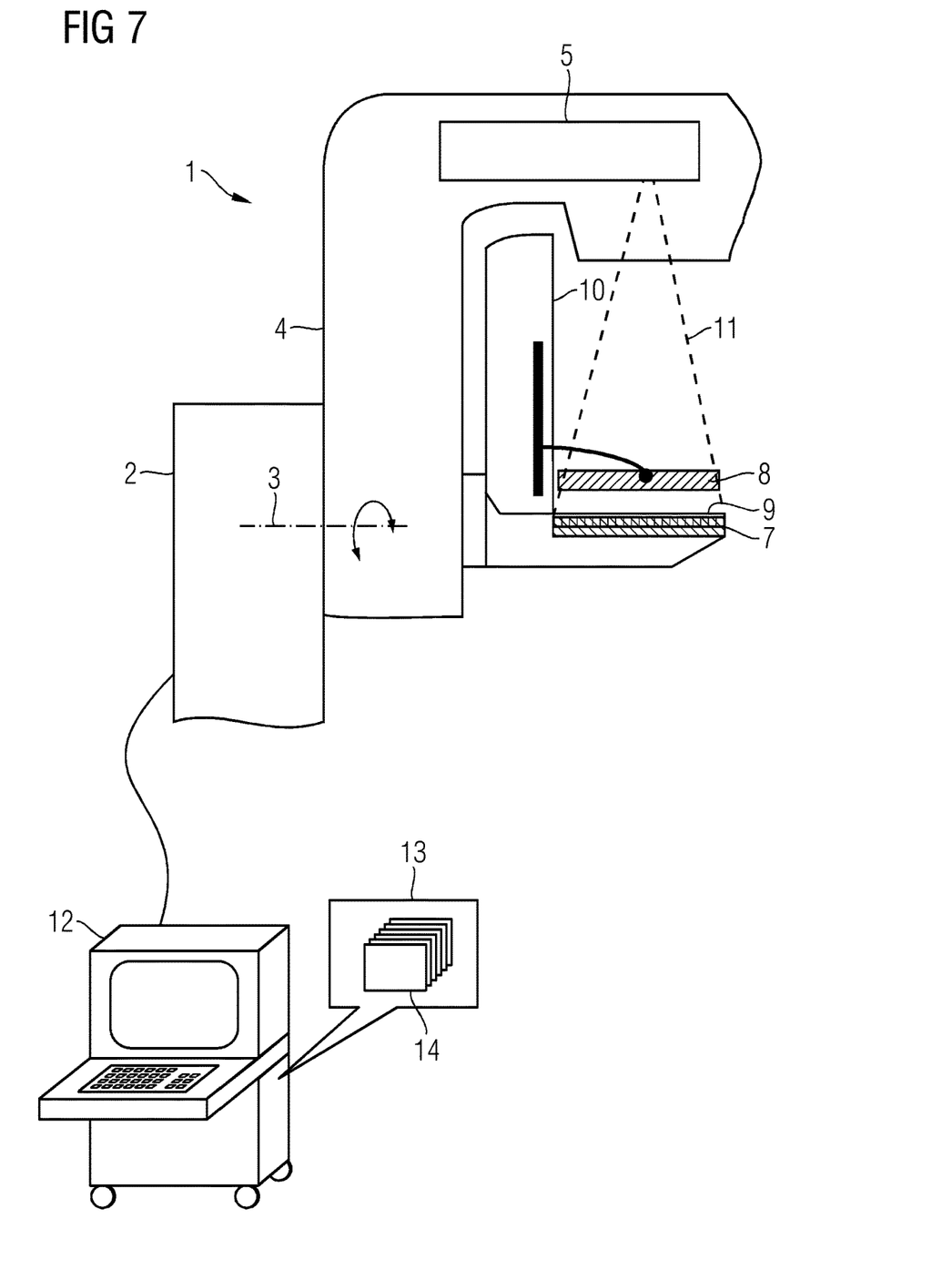
FIG. 7 is an illustration showing the basic construction of the x-ray system for generating projective or tomosynthetic image data of a female breast with spatially structured converting sensor material for generating different absorption spectra in the detector.

In accordance with another embodiment variant of the invention, FIG. 7 again shows a mammography system 1, which in principle corresponds to the mammography system 1 from FIG. 1, although here no spatial spectral filtering is provided, rather the different energy spectra of the image data are realized by a spatially and spectrally different absorption behavior of the sensor material in the detector 7.

Figure 8:
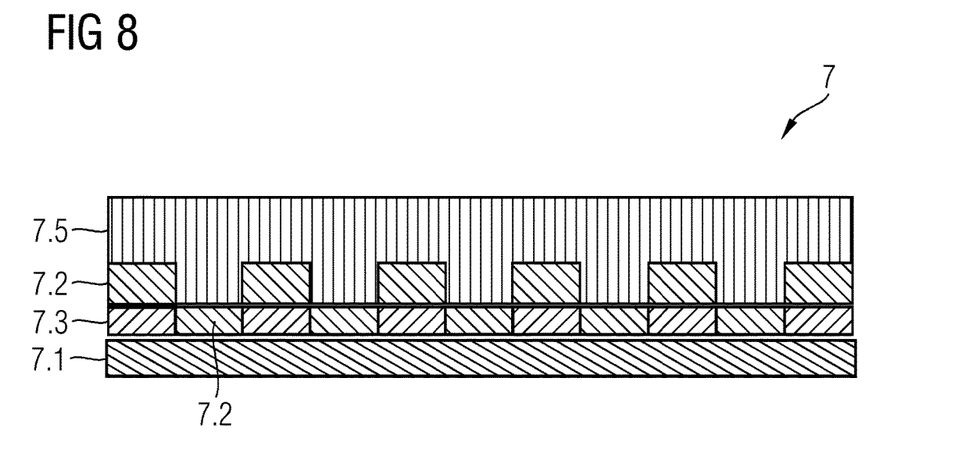
FIG. 8 is a sectional view through a detector constructed in a checkered fashion with sensor layers of different thicknesses distributed over the area for generating pixel-dependently different absorption spectra.
Figure 9:
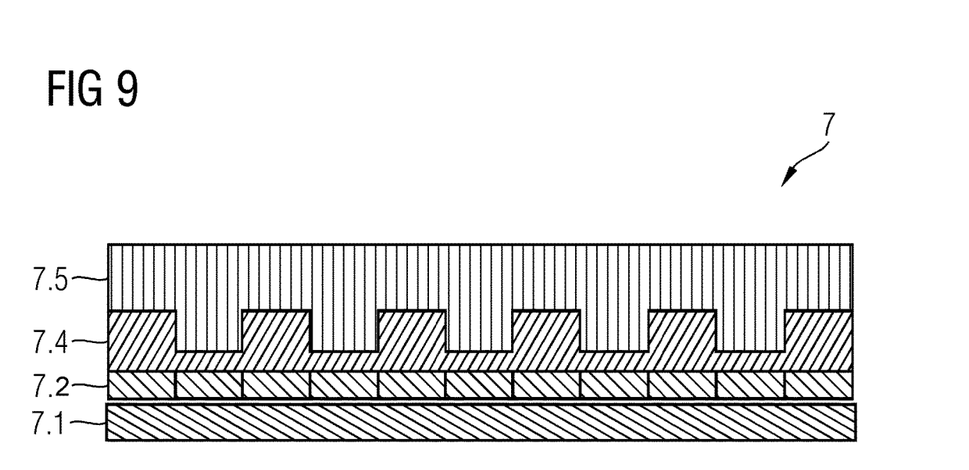
FIG. 9 is a sectional view through the detector constructed in the checkered fashion with sensor layers of different thicknesses distributed over the area for generating pixel-dependently different absorption spectra; and a correspondingly height-structured intermediate layer.

FIGS. 8 and 9 show two variants of a detector construction according to the invention containing height-structured sensor layers.

FIG. 8 schematically shows a cross section through a detector 7, wherein from bottom to top firstly there is arranged a carrier layer 7.1, which can contain electronic conductor tracks, that is to say a TFT panel. Photodiodes 7.2 arranged in a checkered fashion are situated on the carrier layer 7.1, the photodiodes being raised upward by spacer elements 7.3 alternately in the checkered pattern. The height structure thus formed can be followed by the converting sensor layer 7.5, which is embodied in a planar fashion at its top side and thus has pixel by pixel different thicknesses. In accordance with the sensor layer embodied with different thicknesses, a spectrally different absorption behavior is generated, such that depending on the sensor layer thickness different energy spectra are detected in the sensor.

An alternative embodiment of the detector is shown in FIG. 9, in which the thickness structure of the sensor material is produced by a, preferably transparent, intermediate layer. The construction of the detector 7 begins again from bottom to top with a carrier layer 7.1, on which the photodiodes 7.2 are arranged in a checkered fashion in one plane. The intermediate layer 7.4 lies above the photodiodes 7.2 and has a thickness structure that ensures that the sensor layer 7.5 applied thereabove obtains a correspondingly reciprocal thickness structure. By this means, too, a spectrally different absorption behavior is generated pixel by pixel or pixel group by pixel group, as a result of which the energy spectra measured in the individual photodiodes are different. Alternatively, the carrier layer already has a checkered thickness structure; the intermediate layer 7.4 is omitted. In a further alternative embodiment, the sensor layer has a thickness structure facing the radiator, on the basis of a homogeneous carrier and e.g. photodiode.

Figure 10:
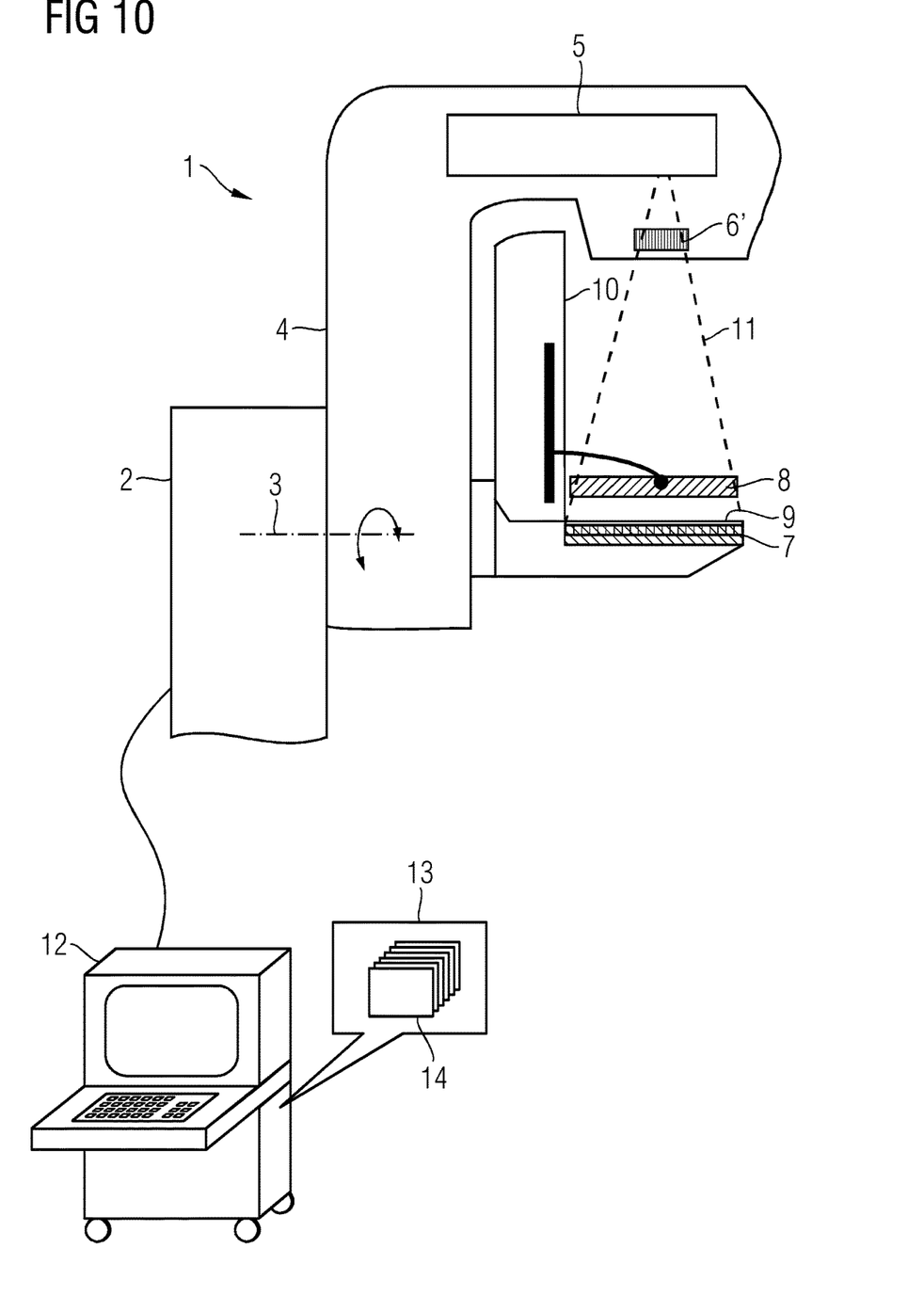
FIG. 10 is an illustration showing the construction of the x-ray system for generating projective or tomosynthetic image data of a female breast with a program for the control according to the invention of the acceleration voltage of the x-ray tube during a scanning.

Finally, FIG. 10 shows another embodiment variant of a mammography system according to the invention, which combines both the variation of the radiation spectrum with the aid of a spatially structured spectral filter 6'—here directly connected to the pivotable x-ray tube 5—arranged in the beam path and a spatially structured sensor material in the detector 7 for generating different absorption spectra. Otherwise the construction of the mammography system 1 corresponds to the exemplary embodiments in FIGS. 1 and 4. Alternatively, it is also possible to use a spectral filter 6 which is arranged directly at the upper compression plate 8. If the spectral filter 6 or 6' is displaced in a coordinated manner according to the pivoting movement of the x-ray tube such that in each case the projection of the thickness structure onto the pixels of the detector 7 remains the same, then a direct tuning of the x-ray radiation spectra used to the absorption spectra can be carried out.

Overall, therefore, the invention discloses a method for the imaging scanning of a female breast in the context of projective digital mammography or tomosynthesis, wherein from a single scanning at least two spatially superimposing images are created on the basis of pixel by pixel or pixel group by pixel group different x-ray energy spectra. In this case, the different x-ray spectra can be generated by locally varying spectral filter, by locally varying spectral absorption or by an acceleration voltage that changes over time multiply during the scanning. Furthermore, an x-ray mammography system is disclosed wherein the radiator-detector system is configured to receive different radiation spectra using a detector divided into a multiplicity of partial areas, such that the data set comprising at least two spatially superimposing imagings on the basis of different x-ray spectra is received with a single scanning, the data set being divided into individual spectrum-specific image data in a second work step. Finally, a pixilated x-ray detector is also disclosed, wherein the converting sensor layer is divided into at least two sets of partial areas having different thicknesses. Within the scope of the invention, the above-mentioned subjects of the invention, taking account of the technical ability of the person skilled in the art, can be combined with the further features and feature combinations disclosed here.

Although the invention has been more specifically illustrated and described in detail by means of the preferred exemplary embodiment, nevertheless the invention is not restricted by the examples disclosed and other variations can be derived therefrom by the person skilled in the art, without departing from the scope of protection of the invention. In particular, the invention is not restricted to the feature combinations indicated hereinafter; rather, it is also possible to form other combinations and partial combinations of the features disclosed which are implementable in an obvious manner for the person skilled in the art.

The invention claimed is:

1. A method for imaging scanning of a female breast in a context of digital projective mammography or tomosynthesis with prefiltered x-ray radiation, which comprises the step of:

generating spectrally different absorption of impinging x-ray radiation on pixel-forming detector elements of a detector at least partially by a sensor layer divided into at least two sets of partial areas which generate individual image pixels, wherein the sets of partial areas have different thicknesses and the sensor layer has a thickness structure defined by the different thicknesses;

creating at least two spatially superimposing images, from a single scanning of the female breast between two compression plates of a mammography system, on a basis of the partial areas receiving pixel-by-pixel or pixel-group-by-pixel-group different x-ray energy spectra.

2. The method according to claim 1, which further comprises generating the at least two spatially superimposing images on the basis of the different x-ray energy spectra on account of different radiation spectra of impinging x-ray radiation impinging on the pixel-forming detector elements of the detector.

3. The method according to claim 2, which further comprises generating the different radiation spectra of impinging x-ray radiation on the pixel-forming detector elements of the detector by, pixel-by-pixel or pixel-group-by-pixel-group, filter layers configured with at least one of different thicknesses or different filter materials.

4. The method according to claim 1, which further comprises generating the at least two spatially superimposing images on the basis of the different x-ray energy spectra on account of different absorption spectra in the pixel-forming detector elements of the detector.

5. The method according to claim 1, which further comprises generating the at least two spatially superimposing images on the basis of the different x-ray energy spectra on account of a combination of different spectra of x-ray radiation impinging on the pixel-forming detector elements of the detector and different absorption spectra in pixels of the detector.

6. The method according to claim 1, which further comprises generating the at least two spatially superimposing images on the basis of different x-ray energy spectra by a variation of x-ray spectrum during the scanning.

7. The method according to claim 6, which further comprises effecting a variation of the x-ray spectrum by multiple variation of an acceleration voltage during the scanning.

8. The method according to claim 1, wherein the imaging scanning is accompanied by a contrast agent administration.

9. The method according to claim 1, wherein from an image originating from the single scanning with image data from the at least two spatially superimposing images on the basis of pixel-by-pixel or pixel-group-by-pixel-group different x-ray energy spectra, a separate image is calculated per x-ray energy spectrum.

10. The method according to claim 9, which further comprises generating separate images, wherein an interpolation method is used for generating the separate images.

11. The method according to claim 9, which further comprises generating separate images by using a method of compressed sensing.

12. An x-ray mammography system for imaging scanning of a female breast in a context of digital projective mammography or tomosynthesis, comprising:
    a programmable control device for an acceleration voltage of an x-ray tube, said programmable control device having a stored program executed during operation, said program performs a method according to claim 1; and
    an x-ray detector including a sensor layer for converting x-ray radiation into light or charge, said sensor layer divided into at least two sets of partial areas, said sets of partial areas having different thicknesses, said sensor layer having a thickness structure defined by the different thicknesses.

13. The method according to claim 1, which further comprises coupling a pixel-by-pixel gain circuit to the thickness structure of the sensor layer.

14. An x-ray mammography system for imaging scanning of a female breast in a context of digital projective mammography or tomosynthesis, comprising:
    a radiator-detector system, containing:
        an x-ray tube having a filter for generating a prefiltered x-ray radiation with a first radiation spectrum;
        a radiation detector including a sensor layer for converting x-ray radiation into light or charge, said sensor layer divided into at least two sets of partial areas which generate individual image pixels, said sets of partial areas having different thicknesses, said sensor layer having a thickness structure defined by the different thicknesses; and
        compression plates including an upper compression plate and a lower compression plate, said compression plates configured for compressing the female breast during scanning;
    said radiator-detector system configured such that the partial areas receive pixel-by-pixel or pixel-group-by-pixel-group different radiation spectra, such that at least two imagings from different x-ray spectra are received with a single scanning of the female breast between said compression plates.

15. The x-ray mammography system according to claim 14, wherein said partial areas of said detector are covered by the pixel-by-pixel or pixel-group-by-pixel-group, differently absorbent radiation filters in relation to the prefiltered x-ray radiation and thereby generate different x-ray energy spectra.

16. The x-ray mammography system according to claim 14, wherein said partial areas of said detector have, pixel-by-pixel or pixel-group-by-pixel-group, sensor layers configured with the different thicknesses, and thereby detect impinging radiation with different absorption spectra.

* * * * *